United States Patent [19]

Lewis

[11] 4,420,229

[45] Dec. 13, 1983

[54] OPHTHALMIC INSTRUMENTS

[75] Inventor: David L. Lewis, Harlow, England

[73] Assignee: Clement Clark International Ltd., England

[21] Appl. No.: 347,564

[22] Filed: Feb. 10, 1982

[30] Foreign Application Priority Data

Feb. 13, 1981 [GB] United Kingdom ................ 8104534

[51] Int. Cl.³ .............................................. A61B 3/02
[52] U.S. Cl. ................................... 351/224; 351/226; 351/243
[58] Field of Search ............... 351/222, 224, 225, 226, 351/237, 239, 243, 244

[56] References Cited

U.S. PATENT DOCUMENTS 4,145,123 3/1979 Krahn ................................. 351/226

Primary Examiner—John K. Corbin
Assistant Examiner—Rodney B. Bovernick
Attorney, Agent, or Firm—Larson and Taylor

[57] ABSTRACT

A Friedmann analyser wtih an arrangement of fixed and rotatable shutters for displaying different patterns of light spots to a subject has a screen for displaying to the operator each light spot pattern selected by illumination of a series of light-emitting elements at fixed positions over the screen area. The light-emitting elements are actuated by a fixed array of infra-red emitting and receiving elements that direct radiation onto a binary-coded reflective pattern displaceable with the rotatable shutter and sense the radiation reflected by said pattern so that with the displacement of the shutter different reflected code signals are sensed associated with respective shutter light patterns displayed to the subject.

8 Claims, 4 Drawing Figures

OPHTHALMIC INSTRUMENTS

BACKGROUND OF THE INVENTION

This invention relates to an ophthalmic instrument for use in testing the vision of a subject.

A known type of instrument for this purpose briefly displays to the subject predetermined patterns of spots of light, the subject indicates what he has seen of these patterns, and from his observations of a number of successive patterns it is possible to characterise particular deficiencies in his field of vision. Examples of such an instrument, known commercially as a Friedmann Analyser, are described in British patent specifications Nos. 925 066 and 2 026 197A.

Because each display pattern is shown only briefly to the subject, e.g. for 1/500th of a second, in order to ensure the subject does not scan the field of vision each time but focusses on a fixed point, only a very limited number of points of light can be included in each pattern, e.g. not more than 4 points each time. This means that a large number of test patterns must be displayed to cover the field of view being examined. In order to assist the task of the operator in recording the results of these many tests, the specification of British patent application No. 2 026 197A describes how the patterns to be displayed can be shown on a screen that is visible only to the operator and not the subject, and the results of the successive tests can be recorded on a chart mounted over that screen.

While the provision of monitoring display for the operator considerably simplifies his task and helps to avoid recording errors, it is found in practice that the means for producing the screen display is not always reliable and that the quality of the screen display is not easily controlled. The present invention is particularly concerned with improving the instrument in these respects.

SUMMARY OF THE INVENTION

According to the invention, in an ophthalmic instrument for displaying to a subject different patterns of light spots in a series of visual tests, the instrument comprising an apertured shutter arrangement for determining the pattern of light spots to be displayed, a member of said shutter arrangement being displaceable to select different light patterns and a screen or like display area being provided on the instrument for displaying to the operator but not the subject each light pattern selected, the means for producing the pattern on said screen comprises a series of light-emitting elements in fixed positions over the area of the screen, said elements being actuated by the use of radiation transmitting means which are arranged to transmit radiation onto reflecting means from which reflected radiation is received by sensing means in dependence upon the movement of the displaceable shutter member, said reflecting means transmitting to said sensing means a different radiation reflection characteristic for each light-spot pattern displayed at the first location and said sensing means responding to the reflected radiation characteristic to actuate the light-emitting elements corresponding to the selected pattern.

In one form of the invention, the reflecting means is movable with the displaceable shutter member for transmission to the sensing means the different reflected radiation characteristics associated with the different light-spot patterns. Additionally or alternatively, there may be masking means for radiation transmission between the transmitting and sensing means movable with the displaceable member for selective exposure of the reflecting means to the radiation.

By producing the operator's screen patterns in these ways, a major source of difficulty is avoided in that the active elements of the means for producing the pattern can all be mounted in fixed positions and the only movable elements are the passive elements that determine the reflection characteristic of the radiation. It is therefore possible to avoid the use of relatively movable electrical contacts which are prone to malfunction over an extended period of use.

According to a preferred feature of the invention, a considerable simplification of the radiation and sensing means is possible by arranging the reflecting means in the form of a coded pattern whereby a series of different reflection characteristics can be generated using a lesser number of radiation sensing means than the number of patterns to be displayed in a test series. As has already been mentioned, a large number of individual patterns must be shown to the subject because of the need to limit the number of light spots in each pattern. A standard series of tests for vision involves a total of 31 light spot patterns and, employing the fibre optics arrangement of patent application No. 2 026 197A for producing the pattern on the operator's screen, a corresponding number of fibre bundles must be provided.

If, however, said reflecting means is arranged to produce a binary-coded reflection characteristic, all the alternatives can be identified using a five-character binary code, so that only five radiation sensing elements are necessary. This can lead to a considerable simplification and, in particular, because the total angular movement of the displaceable shutter member is limited, it makes it easier to dispose the radiation sensing means in a way that reduces any risk of spurious signals through misalignment.

As a convenient and reliable arrangement, infra-red radiation transmitting and sensing elements can be used in the form of units in each of which a sensing element is adapted to receive reflected radiation from an integral emitting element. Radiation frequencies other than in the infra-red range can of course also be employed.

The reflecting means may be economically produced as a patterned coating on one member of the apertured shutter arrangement. Such a coating may be formed by a conventional printed circuit technique and given a final highly reflective surface finish; other possibilities include hot stamping, or direct deposition of a highly reflective material directly onto the shutter surface.

The invention will be described by way of example with reference to the accompanying drawings.

DESCRIPTION OF THE PREFERRED EMBODIMENTS

Figure 1:
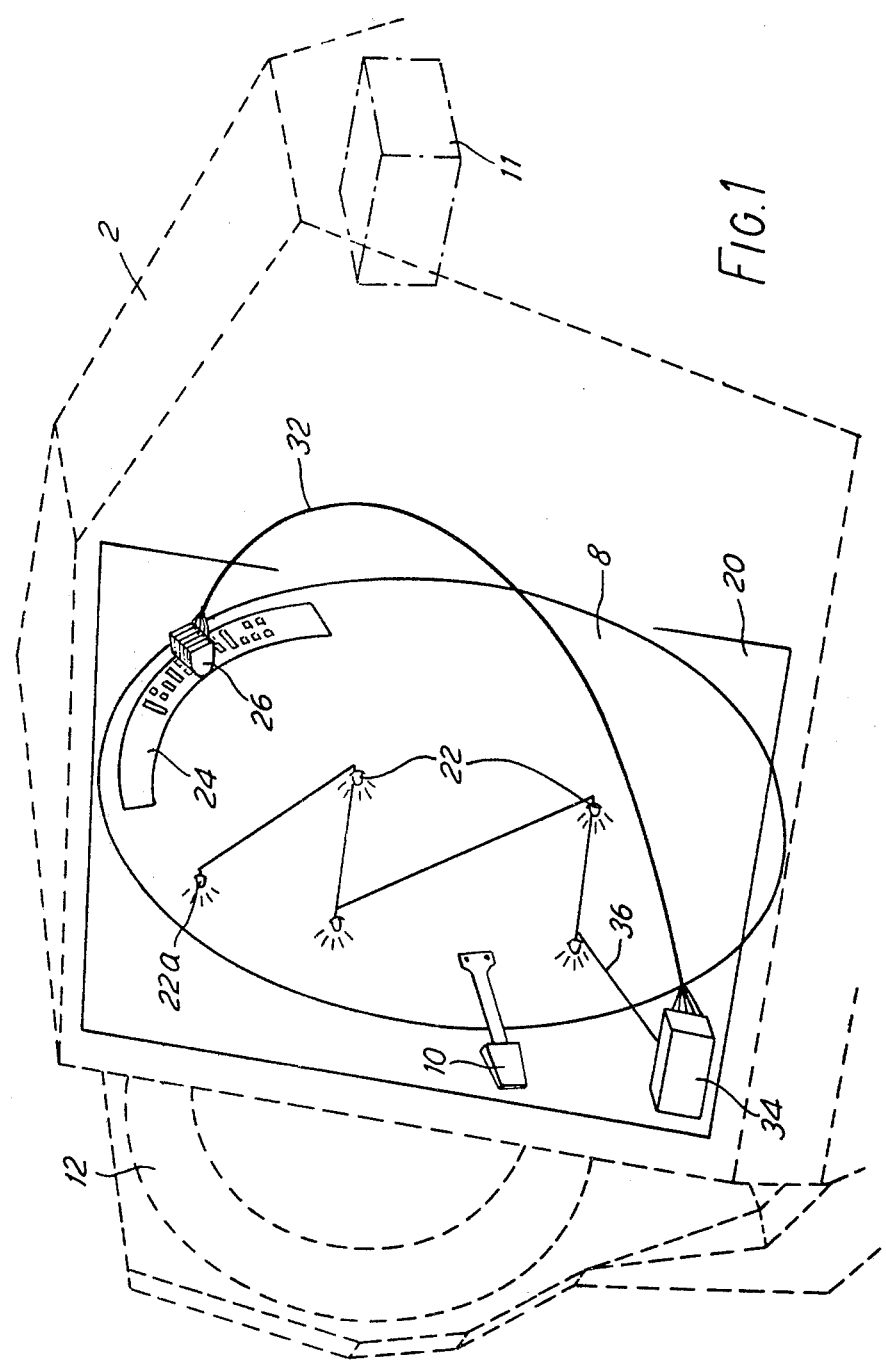
FIG. 1 is a schematic illustration of an instrument according to the invention showing the means for producing the light patterns on the operator's screen.

The instrument comprises a chamber-like housing 2 on the front face of which is an apertured shutter arrangement 4 comprising a pair of discs 6,8 one of which is fixed and the other of which is rotatably mounted at its centre. Both discs have a series of small apertures 4a and as the rotatable shutter disc is turned by its hand grip 10 to prescribed angular positions, different groups of apertures of the two discs will coincide to form particular patterns of openings. Within the housing is a flash tube 11 of known form that is arranged to produce a very brief flash of light with reproducible characteristics, the characteristics being modified if required by the use of adjustable filter means (as described in GB No. 2 026 197A) between the flash tube and the shutter arrangement. When the flash tube is energised, therefore, a pattern of light spots of controlled illumination intensity appears momentarily on the front of the apertured screen arrangement.

The patterns so produced are observed by a subject seated in front of the housing, looking through a backlighting ring 12 that throws its illumination onto the screen arrangement, with his gaze focussed on a fixed marker (not shown) at the centre of the screen arrangement.

At one side of the housing, in a position in which it cannot be seen by the subject, there is a translucent screen 20 visible to the operator, and mounting means adjacent the screen allow the operator to attach a chart (not shown) over it.

On the screen is indicated the pattern of light spots that are to be displayed to the subject when the flash tube is operated. The screen indication is itself in the form of a series of spots of light, but these are produced by a series of light-emitting diodes 22 (only a few of which are illustrated, for clarity) mounted at the required positions immediately under the screen surface and actuated independently of the illumination of the flash tube.

For selecting the diodes 22 to be illuminated, the rotatable shutter disc 8 carries a reflective pattern 24 on its rear face extending over an annular arc 25 of about 90°. The pattern is in the form of five radially spaced binary-coded tracks and operates in conjunction with a group of five infra-red units 26 fixed in the interior of the housing, each unit having an emitting diode 28 directing a constant infra-red beam onto a respective one of the tracks, and a sensor 30 aligned to receive the reflected radiation from the track. The group of infrared units therefore produces a five-bit binary signal that is transmitted by a ribbon cable 32 to a decoding and driving circuit 34 mounted immediately behind the screen 20.

Figure 2:
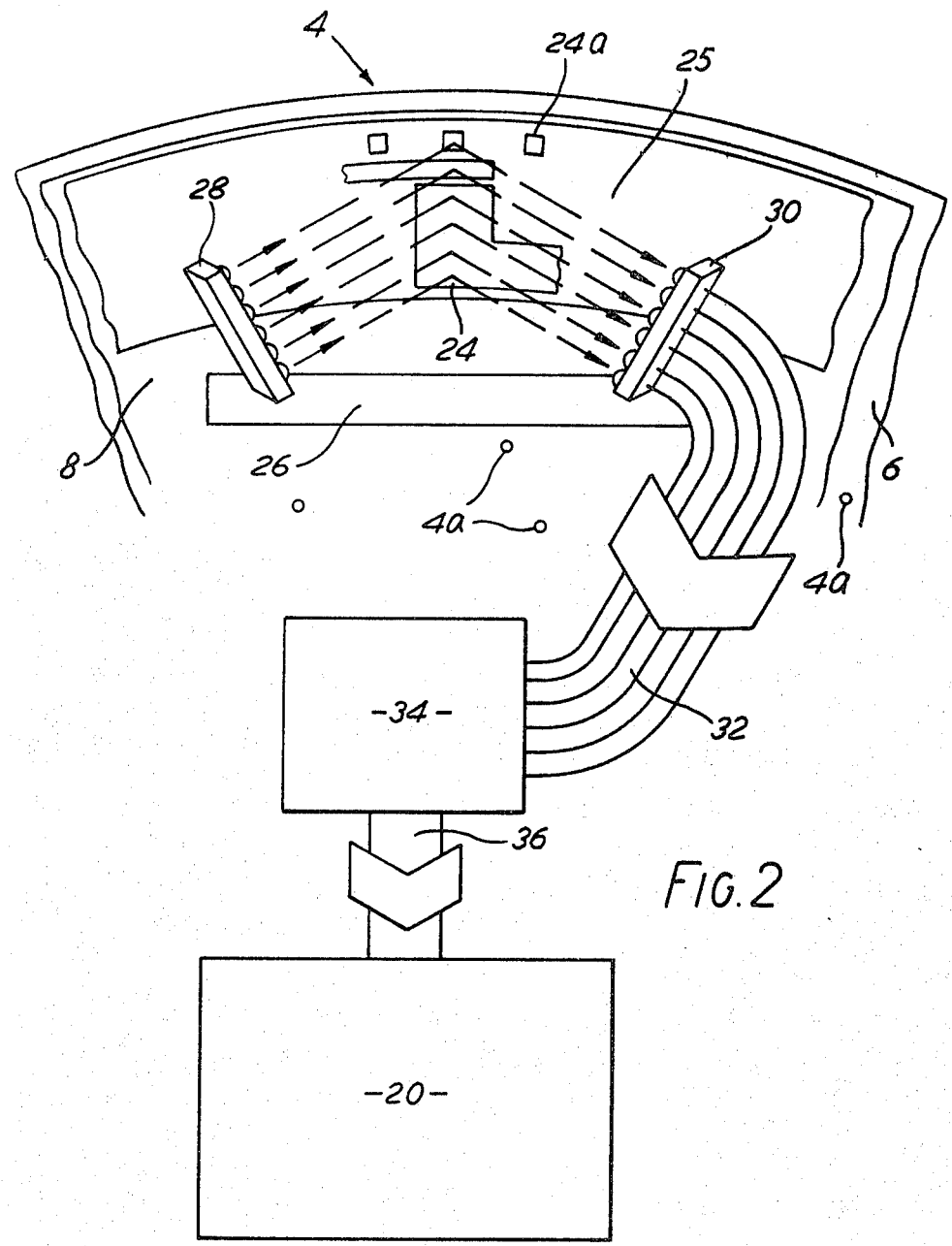
FIG. 2 is a block diagram of the circuit by which the pattern on the operator's screen is produced.

The coded signal signifies the angular position of the rotatable shutter, and therefore is indicative of the selected pattern of spots at that position. FIG. 2 also illustrates a sixth infra red unit associated with a sixth reflective track 24a. This serves simply to switch on the decoding and driving circuit when each test position is reached.

Figure 2A:
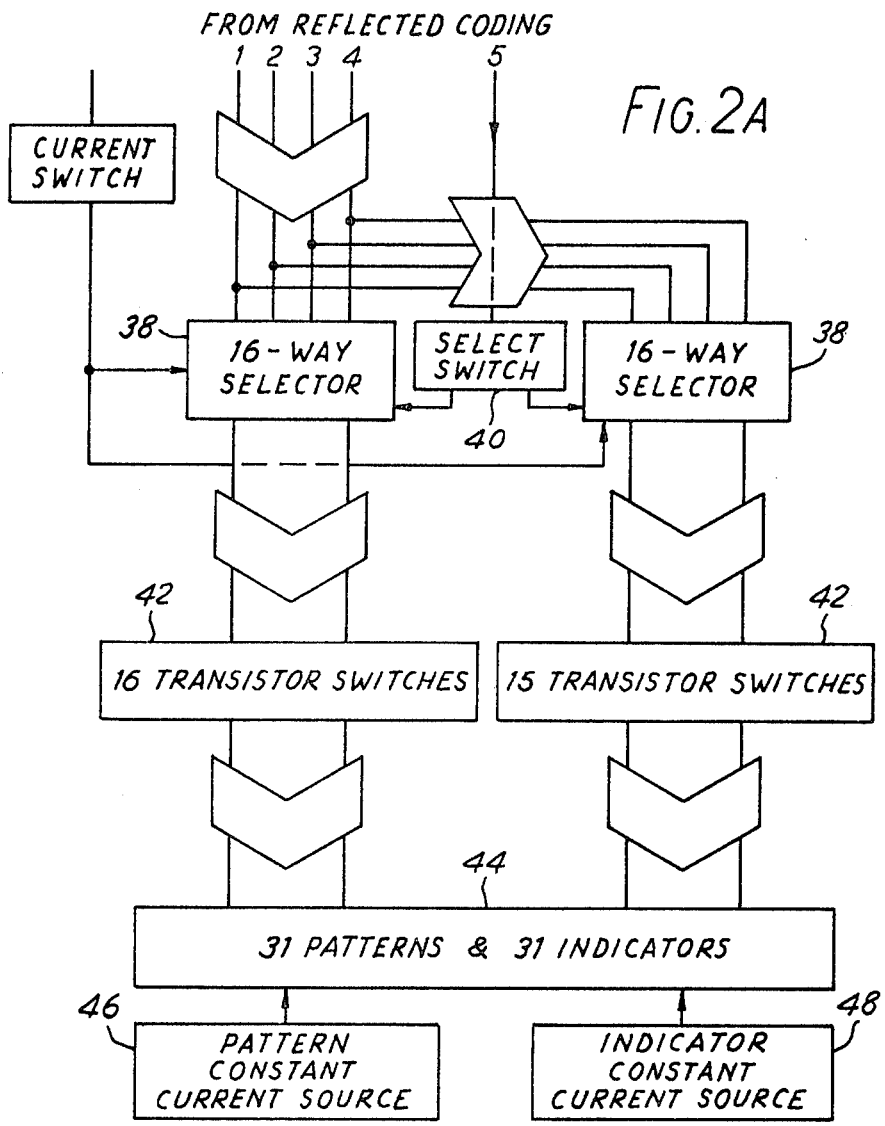
FIG. 2a is a schematic illustration of the decoding and driving circuit of FIGS. 1 and 2.

The decoding and driving circuit can employ generally conventional components and is indicated in schematic outline in FIG. 2a. It comprises two 16-way CD4067 selectors 38 having inputs from four of the coded tracks and also controlled by a select switch 40 actuated by a fifth of the tracks. Respective groups 42 of transistor switches operate a pattern and indicator generating circuit 44 provided with constant current sources 46, 48 for powering the patterns and the indicators. The circuit 44 thus has respective output lines 36 (only one of which is shown in FIG. 1) connected to the different groups of diodes 22 corresponding to the shutter light spot patterns, so that in accordance with the coded signal from the infra red units the illuminated diodes in each case display on the screen 20 the same pattern as that selected for the light spots to be displayed to the subject. The diodes remain illuminated while the apertured screen remains in its set position.

The total number of light patterns used in a standard field-of-vision test is thirty-one. The binary coded signal is thus able to signify all these with only five transmission lines between the infra-red units and the decoding and driving circuit 34, although there will of course be thirty-one output lines from that circuit to the screen diodes. The thirty-second binary-coded signal may be used to hold all the diodes 22 off, this being required when the instrument is being used without its apertured shutter arrangement for light-dark adaptation tests.

When used for field-of-vision tests, the chart secured over the screen can indicate the light spot positions of the patterns to be displayed to the subject, and the illuminated diodes 22 appear at the positions of each selected pattern of spots in turn, so that the operator is left without doubt as to which point on the chart the subject's responses are to be entered.

There may be a further 31 indicator diodes 22a behind the screen that are not part of a pattern of spots but that are illuminated simultaneously with the patterns by the operation of the generating circuit 44 to indicate which pattern is selected. If, for example, along a margin of the chart there is a row of spaces to record the patterns that have been used, these additional diodes can be similarly arranged in a row in register with the individual spaces, and the operator has only to mark the chart each time in the space indicated by the particular diode 22a that has been illuminated.

The reflective pattern 24 on the rotatable shutter is conveniently formed by known printed circuit techniques, e.g. using copper foil. To provide the required degree of reflectivity it can be given a final bright-finish coating, e.g. of nickel. Although illustrated in FIG. 1 as a series of discrete areas, these code elements are preferably linked together as a continuously conductive series so that the nickel coating can be electrodeposited with a single terminal connection to the pattern. Linking of the code elements may not be needed if, for example, they are formed by being deposited directly onto the shutter.

Figure 3:
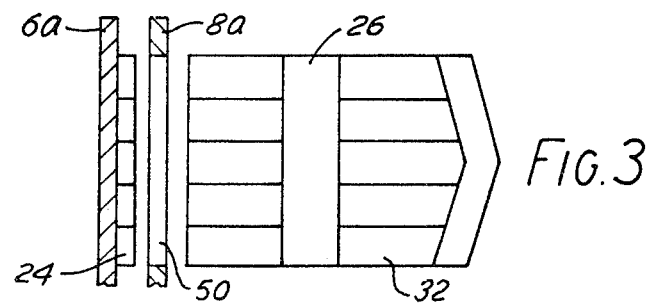
FIG. 3 is a schematic illustration of a modification of the instrument shown in FIGS. 1 and 2.

It may be noted here that it is possible alternatively to dispose the reflective pattern on the fixed shutter, an opening in the rotatable shutter behind it acting as a mask and exposing the appropriate part of the pattern to the radiation transmitting and sensing means as the rotatable shutter moves. This is also the case if the rotatable shutter is in front of the fixed shutter if the latter has a suitable opening in it. FIG. 3 illustrates in outline such an arrangement in which fixed shutter 6a carries the binary-coded reflective pattern 24 and the rotatable shutter 8a has an aperture 50 that selectively masks the coded pattern as the shutter 8a is displaced so that the changed reflection characteristic thereby actuates the appropriate sensing elements of the infra-red units 26.

Although it is preferred to employ a coded signal to produce the light spot illumination of the operator's screen, because of the simplification this can achieve, it is not necessary within the scope of the invention. It is still possible to obtain the increased reliability of the described arrangement, with all the active elements of the signal generating means static and only a passive reflecting member displaceable, if there is a one-to-one correspondence between the number of signal sensors and the number of the spot patterns to be produced. It is also possible to employ other signal producing and transmitting means, e.g. with fibre optics, but the infra-red means described is preferred for economic grounds.

What is claimed is:

1. An ophthalmic instrument for displaying different patterns of light spots in a series of visual tests, the instrument comprising an apertured shutter arrangement at a first location having a series of different settings for determining the pattern of light spots to be displayed at a first location to a subject to be tested, said shutter arrangement comprising fixed and displaceable shutter members and the selection of different light-spot patterns being effected by movement of the displaceable member relative to said fixed member, the instrument further comprising a screen at a second location for displaying each said pattern selected in a manner that is not visible to the subject observing the pattern displayed at said first location, a series of light-emitting elements being disposed in spaced positions over the area of the screen for producing said patterns on the screen, radiation transmitting and sensing means adjacent the apertured shutter arrangement for actuating said light-emitting elements, reflecting means in the path of radiation from said transmitting means for reflecting the radiation to the sensing means, said reflecting means and said radiation transmitting and sensing means being relatively displaceable with said movement of the displaceable shutter member and said reflecting means transmitting to said sensing means a different reflection characteristic for each displayed light-spot pattern associated with a respective setting of the shutter arrangement, actuation means for said light-emitting elements being connected to the radiation sensing means whereby the response of the sensing means to each reflective radiation characteristic actuates the light-emitting elements corresponding to the selected light-spot pattern to display the pattern on the screen at said second location.

2. An instrument according to claim 1 wherein said reflecting means is displaceable with the displaceable shutter member for variation of the reflected radiation characteristic in dependence upon the different positions of the displaceable shutter member.

3. An instrument according to claim 2 wherein the reflecting means is mounted on said displaceable shutter member.

4. An instrument according to claim 1 wherein masking means is disposed in the light path between said reflecting means and said radiation transmitting and sensing means, and said masking means is displaceable with the displaceable shutter member for selective exposure of the reflecting means to produce the different reflective radiation characteristics.

5. An instrument according to claim 1 wherein the reflecting means is in the form of a coded pattern providing a series of different reflection characteristics dependent upon the movement of said displaceable shutter member, and the radiation sensing means comprises a series of radiation sensing elements for respective portions of said coded pattern, there being a lesser number of radiation sensing elements than the number of light-spot patterns to be displayed.

6. An instrument according to claim 5 wherein said reflective means produces a binary-coded reflection characteristic.

7. An instrument according to claim 1, wherein infrared radiation transmitter and detector elements are utilised for the radiation transmitting and sensing means.

8. An instrument according to claim 1, wherein the reflecting means is formed as a patterned coating on one member of the apertured shutter arrangement.

* * * * *